United States Patent [19]
McKenzie

[11] Patent Number: 5,487,745
[45] Date of Patent: Jan. 30, 1996

[54] CURVILINEAR SURGICAL PUNCH

[76] Inventor: Thomas P. McKenzie, 851 Tilden Dr., Lodi, Calif. 95242

[21] Appl. No.: 208,073

[22] Filed: Mar. 7, 1994

Related U.S. Application Data

[63] Continuation of Ser. No. 65,842, May 21, 1993, abandoned.
[51] Int. Cl.⁶ .................................................. A61B 17/32
[52] U.S. Cl. ........................ 606/83; 606/174; 606/184; 30/229
[58] Field of Search ........................... 606/184, 170, 606/171, 167, 83, 174; 128/751; 30/249, 250, 253, 229

[56] References Cited

U.S. PATENT DOCUMENTS

| | | |
|---|---|---|
| D. 289,437 | 4/1987 | Honkanen . |
| 1,754,806 | 4/1930 | Stevenson ........................ 606/174 |
| 2,192,699 | 4/1938 | Storz . |
| 2,541,246 | 7/1948 | Held . |
| 2,930,376 | 3/1958 | Rathmann . |
| 2,990,148 | 2/1991 | Worrick, III . |
| 2,994,321 | 8/1961 | Tischler . |
| 3,391,690 | 7/1968 | Armao . |
| 3,835,860 | 9/1974 | Garretson . |
| 4,243,047 | 1/1981 | Olsen ........................ 128/751 |
| 4,545,374 | 10/1985 | Jacobson . |
| 4,662,371 | 5/1987 | Whipple et al. . |
| 4,712,545 | 12/1987 | Honkanen . |
| 4,944,093 | 7/1990 | Falk ........................ 606/174 X |
| 4,971,067 | 11/1990 | Bolduc et al. . |
| 4,976,269 | 12/1990 | Mehl . |
| 4,986,825 | 1/1991 | Bays et al. . |
| 5,219,357 | 6/1993 | Honkanen et al. ........ 128/751 X |

FOREIGN PATENT DOCUMENTS

| | | |
|---|---|---|
| 0401728 | 6/1990 | European Pat. Off. . |
| 361907 | 12/1906 | France ........................ 606/174 |
| 1037403 | 4/1943 | France . |
| 245402 | 4/1912 | Germany ........................ 606/174 |
| 3303349 | 8/1984 | Germany . |
| 9208415 | 5/1992 | WIPO . |

OTHER PUBLICATIONS

Acufex Microsurgical, Inc.; Acufex Rotary Instruments.
Arthrotek; "Precision Hand Instrumentation"; 1990; Biomet, Inc.
Acufex Microsurgical, Inc.; "The Acufex Duckbill Punch"; 1987.
Acufex Microsurigal Inc.; "Scoop, Blunt Nose, etc."; 1987.
Acufex Microsurgical, Inc., "The One–Piece Disposable Knife"; 1986.

*Primary Examiner*—Michael H. Thaler
*Attorney, Agent, or Firm*—John P. O'Banion

[57] ABSTRACT

A curvilinear surgical punch (10) having a cutting head (21) for performing surgery upon the meniscal tissue of the knee joint is disclosed herein. Cutting head (21) includes an upper blade member (22) pivotal upon a lower frame member (24). Upper blade member (22) and lower frame member (24) both include arcuate cutting edges (26) and (28), respectively. The arcuate cutting edges of the present invention can be adapted toward a variety of configurations and sizes for operating upon different areas of the meniscal tissue.

12 Claims, 6 Drawing Sheets

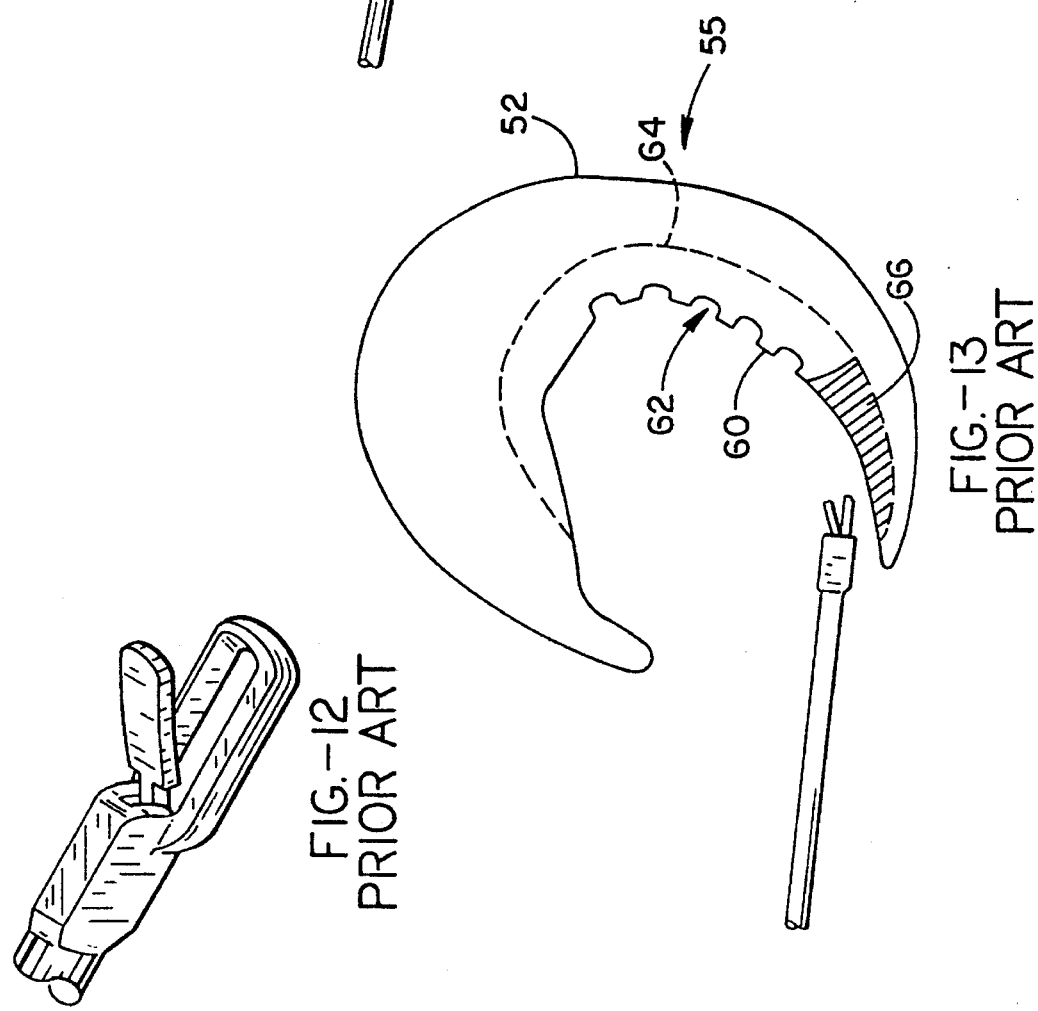

CURVILINEAR SURGICAL PUNCH

CROSS-REFERENCE TO RELATED APPLICATIONS

This is a continuation of application Ser. No. 08/065,842 filed on May 21, 1993 now abandoned.

BACKGROUND OF THE INVENTION

1. Field of the Invention

This invention pertains to surgical instruments generally and, more particularly, to a manually operated curvilinear surgical punch for trimming meniscal tissue and achieving a smooth cut surface thereupon.

2. Description of the Background Art

The advent of arthroscopic surgery greatly simplified surgical procedures performed upon the knee. Arthroscopy enabled surgery to be performed inside the knee, using a minor-invasive technique involving operating through small holes cut into the knee. Previously, the entire knee joint had to be surgically opened and invaded, thereby increasing the potential for infection, and requiring the patient to endure a long convalescence.

A particularly common facet of arthroscopic surgery involves operating upon the meniscal tissue inside the knee. The meniscus is a fibrous, cartilaginous, tissue, prevalent in the knee joint, which serves a shock absorption function inside the knee, thereby continuously protecting the knee joint from damage. As a result of acute injury or continuous wear upon the meniscus while performing its shock absorption function, the meniscus often degrades, becoming ragged and torn at the edges in the process. When the meniscus degrades, the ragged edges can abrade inside the knee joint, causing irritation, and necessitating surgery to remove the ragged edges. A goal in designing instruments for meniscal tissue surgery has been to achieve a design which cleanly debrides the degenerative meniscal tissue to a smooth, curved meniscal remnant. A meniscal remnant with a smooth surface eliminates abrasion within the knee joint, thereby eliminating irritation caused to the patient, following surgery.

Heretofore, a variety of surgical instruments have been developed which trim meniscal tissue to varying degrees of smoothness. These instruments have been of three primary types: (i) manually operated cutting instruments, including punch-type instruments; (ii) motorized trimming instruments; and (iii) laser surgery instruments. The punch-type instruments devised to date have suffered from inherent limitations in achieving sharp, clean, smooth, meniscal remnants and also require numerous passes to achieve a reasonably smooth meniscal remnant. The motorized instruments produce smooth meniscal remnants, but also require a multitude of passes to achieve this result. The laser instruments provide a smooth surface with a minimal amount of surgical passes; however, their high operating expense has proven to be a negative factor in their application to meniscal surgery. Therefore, there still exists a need for an instrument which can achieve an exceptionally smooth meniscal remnant, while requiring as few passes as possible, with the least expense, to achieve this favorable result.

The present invention achieves superior results in obtaining smooth meniscal remnants over previous instruments by employing a curvilinear cutting surface having a long, sweeping curve length. This long curve length allows the surgeon to achieve a smooth meniscal remnant in one or two passes with the instrument, thereby reducing the time required for meniscal trim surgery. Previous meniscal surgery instruments do not possess curvilinear cutting surfaces equivalent to the present invention disclosed herein.

For example, U.S. Pat. No. 2,994,321 issued to Tischler on Aug. 1, 1961, discloses a biopsy punch for taking tissue samples. This instrument has a set of jaws comprised of a top and a bottom cutting surface which are closeable upon each other. The cutting surfaces are tapered towards their ends in a "boat bottom" shape. U.S. Pat. No. 3,391,690 issued to Armao on Jul. 9, 1968, discloses a biopsy punch having a set of jaws comprised of a pair of closeable cutting surfaces. The cutting surfaces may be of a variety of shapes, including elliptical shapes.

A trade brochure published by Acufex Microsurgical Inc., discloses several manually operated instruments which are applicable to meniscal surgery procedures. One such instrument is a hooked rotary scissors with a slightly curved cutting surface. This instrument can be manufactured in left and right configurations for operating upon the left and right meniscus, respectively. The Acufex publication also discloses a scissor punch which can be manufactured in straight and upcurving configurations. In addition, a variety of single-bladed "meniscectomy" knives having a plurality of shapes are shown. A trade brochure published by Arthrotek discloses a variety of elliptical meniscal punches which are designed specifically for achieving smoother meniscal remnants. The width of the elliptical portions of these punches is a maximum of 3.4 mm.

U.S. Pat. No. 4,662,371 issued to Whipple et al. on May 5, 1987, discloses a surgical instrument used for meniscal surgery comprised of an elliptical punch having a top surface which closes upon a bottom surface. This instrument also has a suction means for removing severed meniscal tissue from the knee joint. U.S. Pat. No. 4,971,067 issued to Bolduc et al. on Nov. 20, 1990, as well as U.S. Pat. No. 4,986,825 issued to Bays et al. on Jan. 22, 1991, both disclose surgical instruments having U-shaped cutting surfaces. U.S. Pat. No. 2,930,376 issued to Rathmann on Mar. 29, 1960, discloses a surgical instrument having a triangular cutting surface. U.S. Pat. No. 2,192,699 issued to Storz on Mar. 5, 1940, discloses a surgical instrument having closeable jaws, the jaws having convex surfaces for removing circular sections of tissue. U.S. Pat. No. 3,835,860 issued to Garretson on Sep. 17, 1974, discloses a surgical bone punch for cutting and shaping bone or cartilaginous tissue. U.S. Pat. No. 4,990,148 issued to Worrick, III et al. on Feb. 5, 1991, discloses a rongeur which can be used for removing tissue from the vertebrae or knee. U.S. Pat. No. 2,541,246 issued to Held on Feb. 13, 1951, discloses a surgical instrument for cutting muscle tissue. U.S. Pat. No. 4,545,374 issued to Jacobson, discloses a surgical instrument for performing a lumbar diskectomy. U.S. Pat. No. 4,976,269 issued to Mehl, on Dec. 11, 1990, discloses a tissue needle for extracting a biopsy sample. U.S. Pat. No. 4,712,545 issued to Honkanen on Dec. 15, 1987, discloses a surgical instrument having a pair of cutting jaws adapted for removing tissue. U.S. Pat. No. D-289,437 issued to Honkanen on Apr. 21, 1987, discloses a design for a combined handle and shank for a surgical instrument.

The foregoing patents disclose a variety of surgical instruments which are designed for removing meniscal, or other tissue. Several of the previous designs also disclose surgical instruments having elliptically curved cutting surfaces, but none disclose the long, sweeping, curvilinear cutting surface of the present invention. The configuration of the curvilinear surgical punch disclosed herein provides for smoother meniscal trims, with fewer passes, than previous designs. The smoothness of the resulting meniscal remnant causes less irritation to the patient and by employing the present invention, fewer passes are required to achieve a smooth meniscal remnant, which reduces the time required for meniscal surgery.

The foregoing patents and publications reflect the state of the art of which the applicant is aware and are tendered with the view toward discharging applicant's acknowledged duty of candor in disclosing information which may be pertinent in the examination of this application. It is respectfully stipulated, however, that none of these patents or publications, teach or render obvious, singly or when considered in combination, applicant's claimed invention.

SUMMARY OF THE INVENTION

This invention pertains to a curvilinear surgical punch for meniscal trim surgery which greatly improves the smoothness of the meniscal remnant created. The smooth meniscal remnant created by the present invention is achieved with a minimal amount of passes of the curvilinear cutting surface upon the meniscal tissue.

By way of example, and not of limitation, the curvilinear surgical punch disclosed herein includes a support means having a length and attitude sufficient for probing within a body cavity. At one end of the support means is a means for operating the curvilinear surgical punch and, at the opposite end, is a curvilinear cutting surface used for trimming meniscal tissue.

An additional feature of the curvilinear surgical punch disclosed herein, is that it achieves a smooth meniscal remnant in one or two passes upon the meniscal tissue. Previous meniscal surgical instruments have characteristically required that numerous passes be performed along the meniscus to achieve a smooth meniscal remnant, which increases the time required for surgery. The present invention decreases the time required for surgery.

An object of the invention is to provide a surgical punch having a long curvilinear cutting surface.

Another object of the invention is to provide a curvilinear surgical punch which creates a meniscal remnant having an exceptionally smooth surface.

Another object of the invention is to provide a curvilinear surgical punch which is inexpensive to manufacture and operate.

Still another object of the invention is to provide a curvilinear surgical punch which reduces the time required for meniscal trim surgery.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 12 is a perspective view of a prior art punch-type surgical instrument.

FIG. 13 is a diagrammatic view showing the prior art instrument of FIG. 12 trimming a portion of meniscal tissue.

FIG. 14 is a diagrammatic view showing the present invention trimming a portion of meniscal tissue.

DESCRIPTION OF THE PREFERRED EMBODIMENTS

Figure 1:
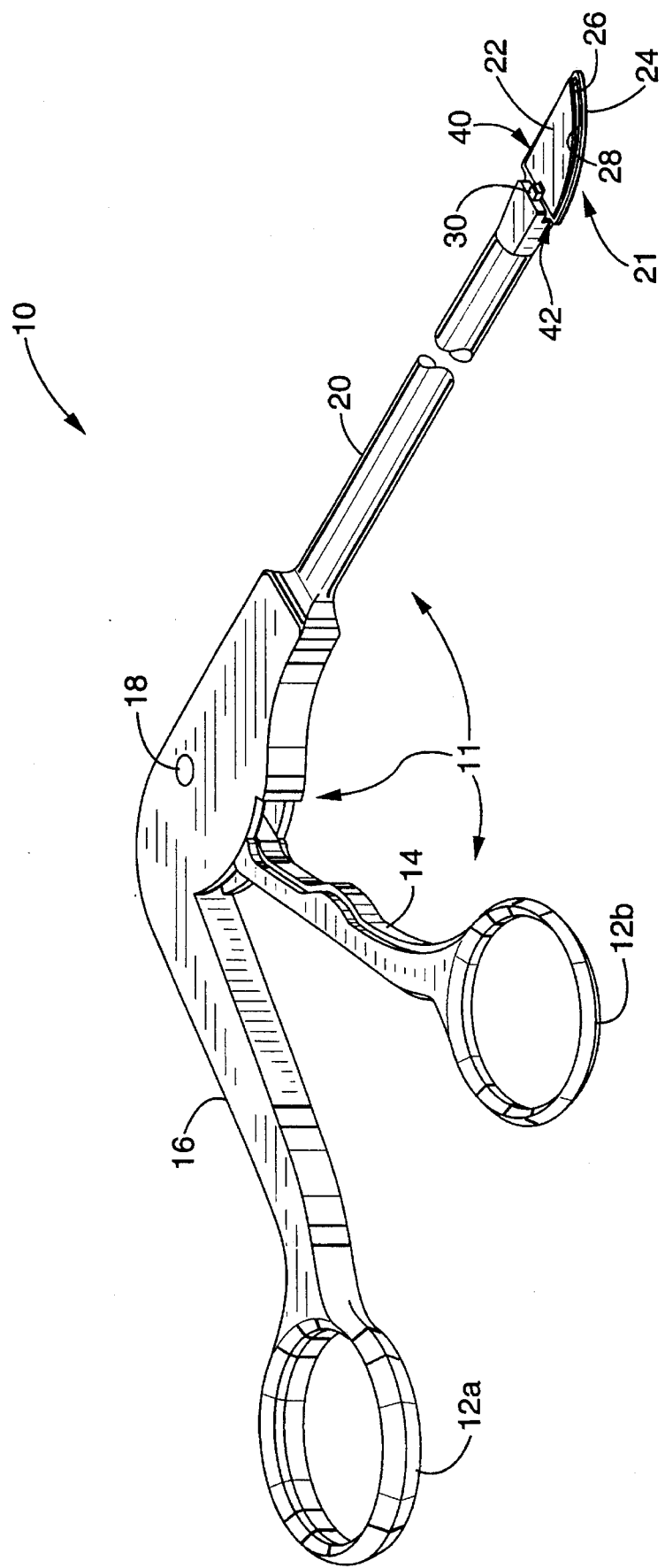
FIG. 1 is a perspective view of the apparatus of the present invention showing the cutting mechanism coupled to a typical actuating means.

Referring more specifically to the drawings, for illustrative purposes the present invention is embodied in the apparatus generally shown in FIG. 1, and more specifically shown in FIG. 2 through FIG. 10. It will be appreciated that the apparatus may vary as to configuration and as to details of the parts without departing from the basic concepts as disclosed herein.

FIG. 1 illustrates generally, a curvilinear surgical punch 10 of the present invention. The curvilinear surgical punch 10 includes actuating means 11 which, in the preferred embodiment, comprises a pair of ring handles 12a, 12b pivotally coupled to fulcrum point 18 by arms 14 and 16. Support means 20 extends from arm 16 at one end and, at a second end, support means 20 is coupled to a cutting head 21 having an upper blade member 22 and a lower frame member 24. Coupled to arm 14 and extending through support means 20 is a link coupling (not shown) which is operatively coupled to cutting head 21. It should be noted that the particular configuration of actuating means 11 is not critical to the present invention, and that alternative configurations can be employed.

Figure 2:
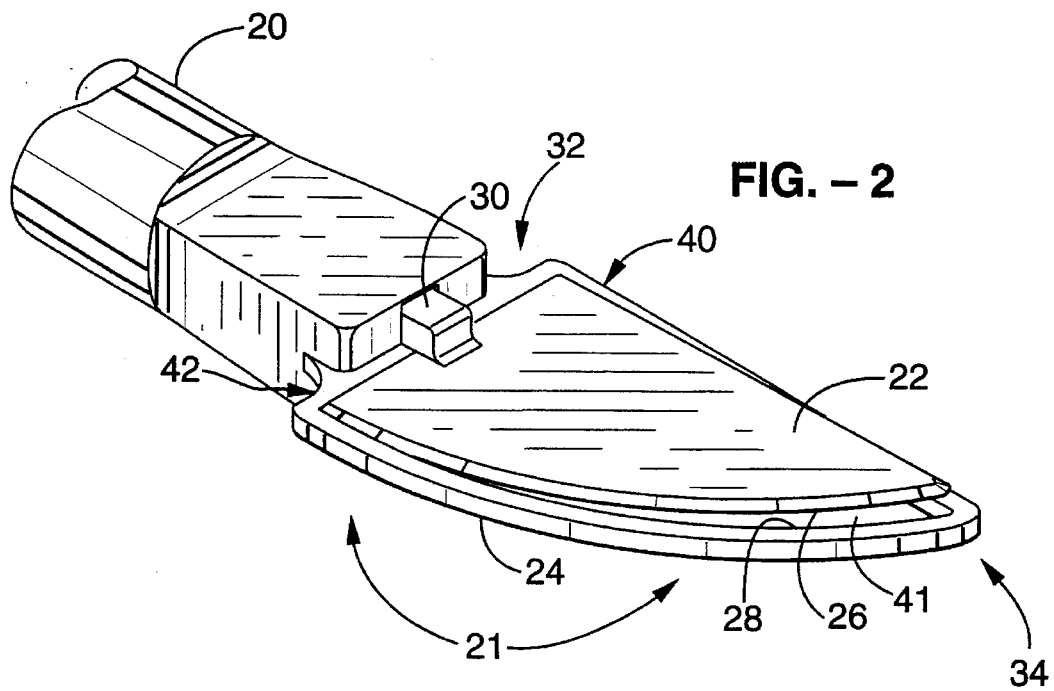
FIG. 2 is a perspective view of a cutting mechanism employed in the present invention, which shows an aligned orientation of the cutting mechanism in relation to the support structure, and the upper blade member in a partially open position in relation to the lower frame member.
Figure 3:
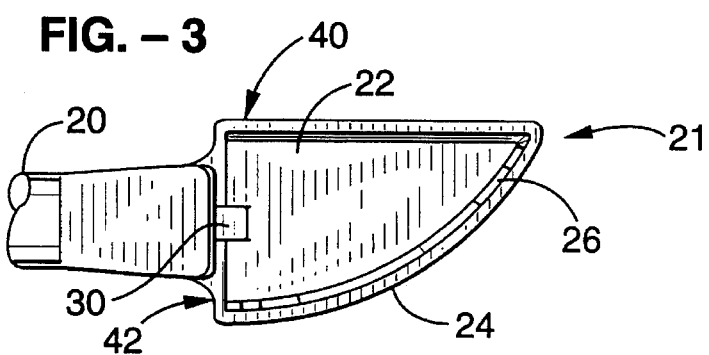
FIG. 3 is a plan view of the cutting mechanism of FIG. 2.
Figure 4:
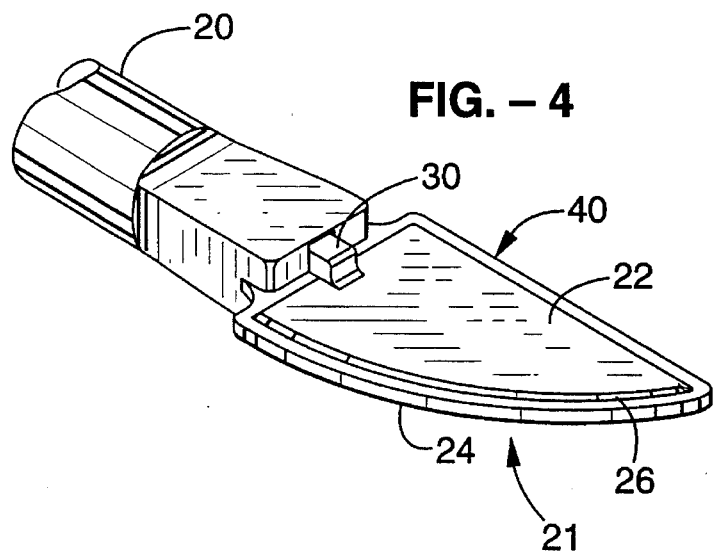
FIG. 4 is a perspective view of the cutting mechanism of FIG. 2 showing the upper blade member in a closed position in relation to the lower frame member.

Referring also to FIG. 2 through FIG. 4, which show with more specificity the cutting head 21 of the present invention, in the preferred embodiment cutting head 21 includes an upper blade member 22 which is pivotally coupled to a lower frame member 24 at pivot point 30. By operating actuating means 11, upper blade member 22 articulates in relation to frame member 24 by pivoting at pivot point 30.

Referring now to FIG. 2 through FIG. 4, it can be seen that the upper blade member 22 and lower frame member 24 have a proximal end 32 and a distal end 34 in relation to the support means 20. Upper blade member 22 and lower frame member 24 are coupled at their proximal ends 32 to support means 20. Upper blade member 22 also has a central longitudinal axis extending between its proximal and distal ends and a central lateral axis extending from an arcuate cutting edge 26 to an opposite side 40 of the cutting head 21 which also includes a cutting edge. The central longitudinal and lateral axes intersect each other at a point of intersection. Arcuate edge 26 is preferably convex in shape, being formed in a radial arc extending outwardly from the point of intersection of the two axes of upper blade member 22. It is this arcuate edge 26 which designates the curvilinear feature of this invention. Arcuate edge 26 serves as the primary cutting edge, and is located substantially laterally in relation to support means 20, such that in the preferred embodiment, the majority of arcuate edge 26 extends outwardly from support means 20. Arcuate edge 26 must be substantially lateral in relation to support means 20 so that support means 20 does not interfere with the ability of arcuate edge 26 to contact body tissue.

Lower frame member 24 includes a cavity 41 consisting of an open space in which upper blade member 22 communicates. In an alternative embodiment, cavity 41 can be a chamber having a volume sufficient to contain a quantity of severed meniscal tissue. Lower frame member 24 has an arcuate edge 28, similar to arcuate edge 26, which denotes a portion of the periphery of cavity 41. In operation, a portion of meniscal tissue is placed between the arcuate edges 26 and 28 of upper blade member 22 and lower frame member 24, respectively. Next, referring again to FIG. 1, operating means 11 is engaged, which allows upper blade member 22 to articulate in relation to lower frame member 24 at pivot point 30, thereby closing upon lower frame member 24, which allows arcuate edges 26 and 28 to communicate closely, thereby severing any meniscal tissue caught between them. The severed meniscal tissue passes through cavity 41 in lower frame member 24, thereby clearing cutting head 21 of meniscal tissue, which prepares the instrument for another cut. The severed meniscal tissue can then be removed from the knee joint by suction means or some other suitable method.

The curve length of the arcuate edges 26 and 28 is important in allowing the curvilinear surgical punch 10 of the present invention to achieve a smooth meniscal remnant in no more than two surgical passes upon the degraded meniscal tissue. The curve length of arcuate edges 26 and 28 is defined as the length of arcuate edges 26 and 28 extending between proximal ends 32 and distal ends 34 of upper cutting member 22 and lower frame member 24, respectively.

The curvilinear surgical punches of the present invention can be manufactured in a plurality of shapes and configurations, depending upon the application desired. Several preferable shapes and configurations have been determined to offer advantages in performing surgery on specific areas of the meniscus, these preferable shapes being depicted in FIG. 2 through FIG. 10. In the following discussion regarding the advantages of using the "standard" "sidebiting" or "tomahawk" embodiments of the present invention, which are depicted in FIG. 2 through FIG. 4, FIG. 5 through FIG. 7, and FIG. 8 through FIG. 10, respectively, it is necessary to refer also to FIG. 11, which is a representation of a human right knee joint showing the lateral meniscus 50 and the medial meniscus 52 divided into anterior third 54, middle third 55, and posterior third 56.

The standard curvilinear surgical punch of FIG. 2 through FIG. 4 would be especially suited for operating upon the anterior third 54 of the meniscus. Note that, in the embodiment of FIG. 2 through FIG. 4, the cutting head 21 is axially aligned longitudinally with the support means 20. In addition, the standard curvilinear surgical punch shown in FIG. 2 through FIG. 4 could be manufactured in a left or a right configuration for operating upon the medial and lateral meniscus, depending upon which knee is undergoing surgery. In other words, the position of the arcuate edges 26, 28 can be rotated one hundred and eighty degrees.

Figure 5:
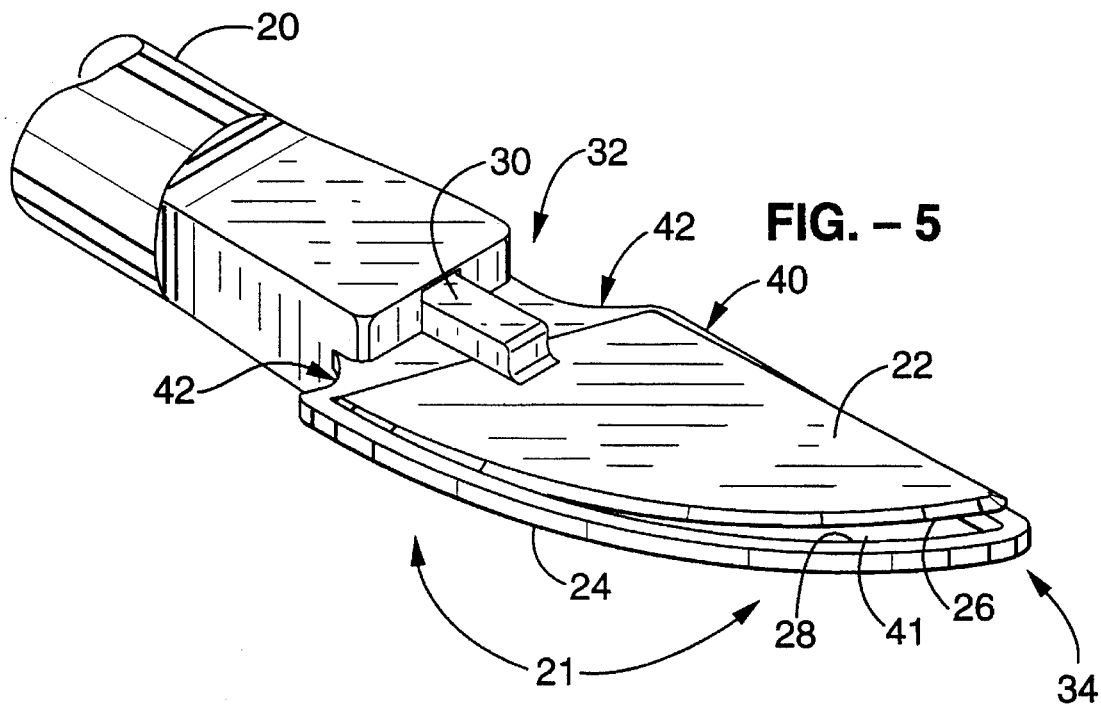
FIG. 5 is a perspective view of an alternative embodiment of the cutting mechanism of FIG. 2, which shows an offset orientation of the cutting mechanism in relation to the support structure, and the upper blade member in a partially open position in relation to the lower frame member.
Figure 6:
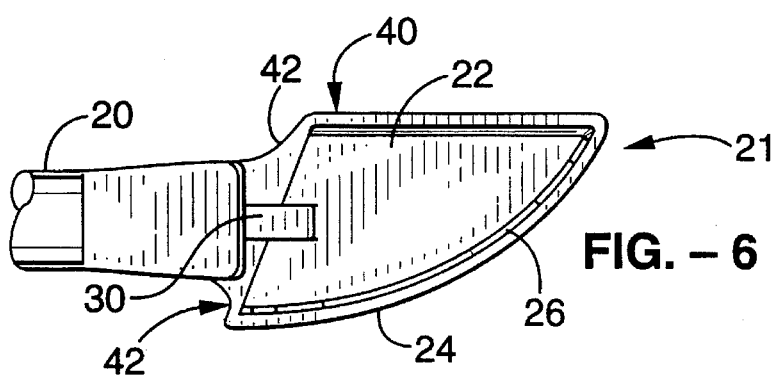
FIG. 6 is a plan view of the cutting mechanism of FIG. 5.
Figure 7:
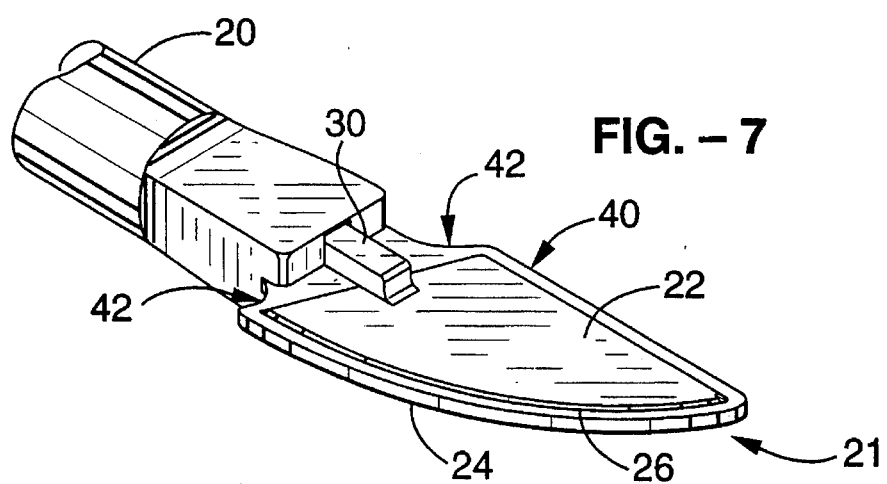
FIG. 7 is a perspective view of the cutting mechanism of FIG. 5 showing the upper blade member in a closed position in relation to the lower frame member.

Referring to FIG. 5 through FIG. 7, the sidebiting embodiment of the curvilinear surgical punch of the present invention is presented. This embodiment is essentially the same as that shown in FIG. 2 through FIG. 4, except that the cutting head 21 is angularly offset laterally in comparison to the longitudinal axial alignment of the cutting head in FIG. 2 through FIG. 4. Referring again to FIG. 11, the sidebiting punch is adapted mainly for operating upon the posterior third 56 of the lateral and medial meniscus 50 and 52, respectively. The sidebiting curvilinear punch could be manufactured in left and right configurations for operating upon the medial and lateral meniscus, depending upon which knee is undergoing surgery. FIG. 5 through FIG. 7 shows how sides 40 and 42 of the cutting head are not perpendicular as in the standard curvilinear surgical punch of FIG. 2 through FIG. 4. Instead, sides 40 and 42 have a pronounced angle spanning their intersecting corner. The size of the angle is limited only by the practical requirements of the invention, and can be obtuse, right, or acute, but a range of 110 degrees to 135 degrees is preferable. The angle applied between sides 40 and 42 allows the sidebiting shape to conform to the anterior third 54 and posterior third 56 of lateral meniscus 50 or medial mensicus 52 in a superior fashion.

Figure 8:
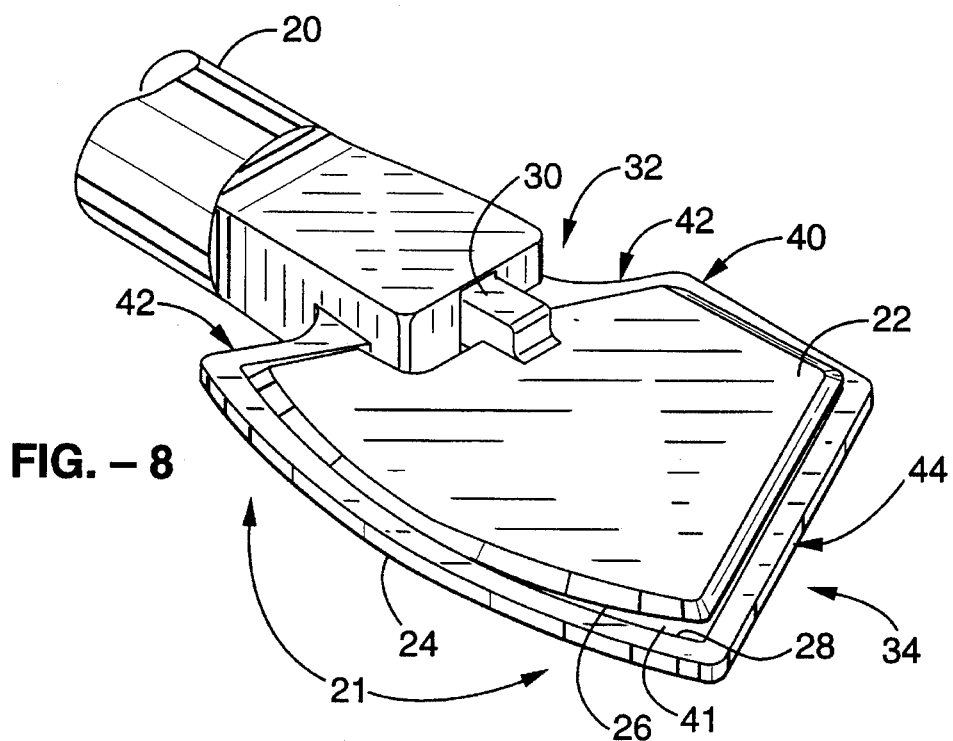
FIG. 8 is a perspective view of an alternative embodiment of the cutting mechanism employed in the present invention, and shows the upper blade member in a partially open position in relation to the lower frame member.
Figure 9:
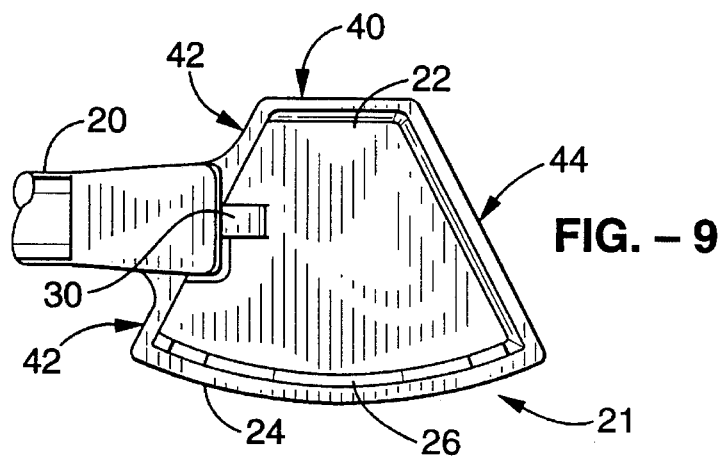
FIG. 9 is a plan view of the cutting mechanism of FIG. 8.
Figure 10:
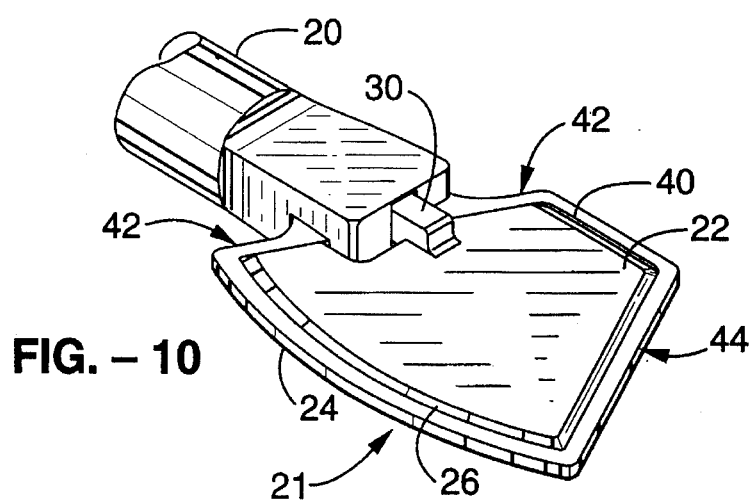
FIG. 10 is a perspective view of the cutting mechanism of FIG. 8 showing the upper blade member in a closed position in relation to the lower frame member.
Figure 11:
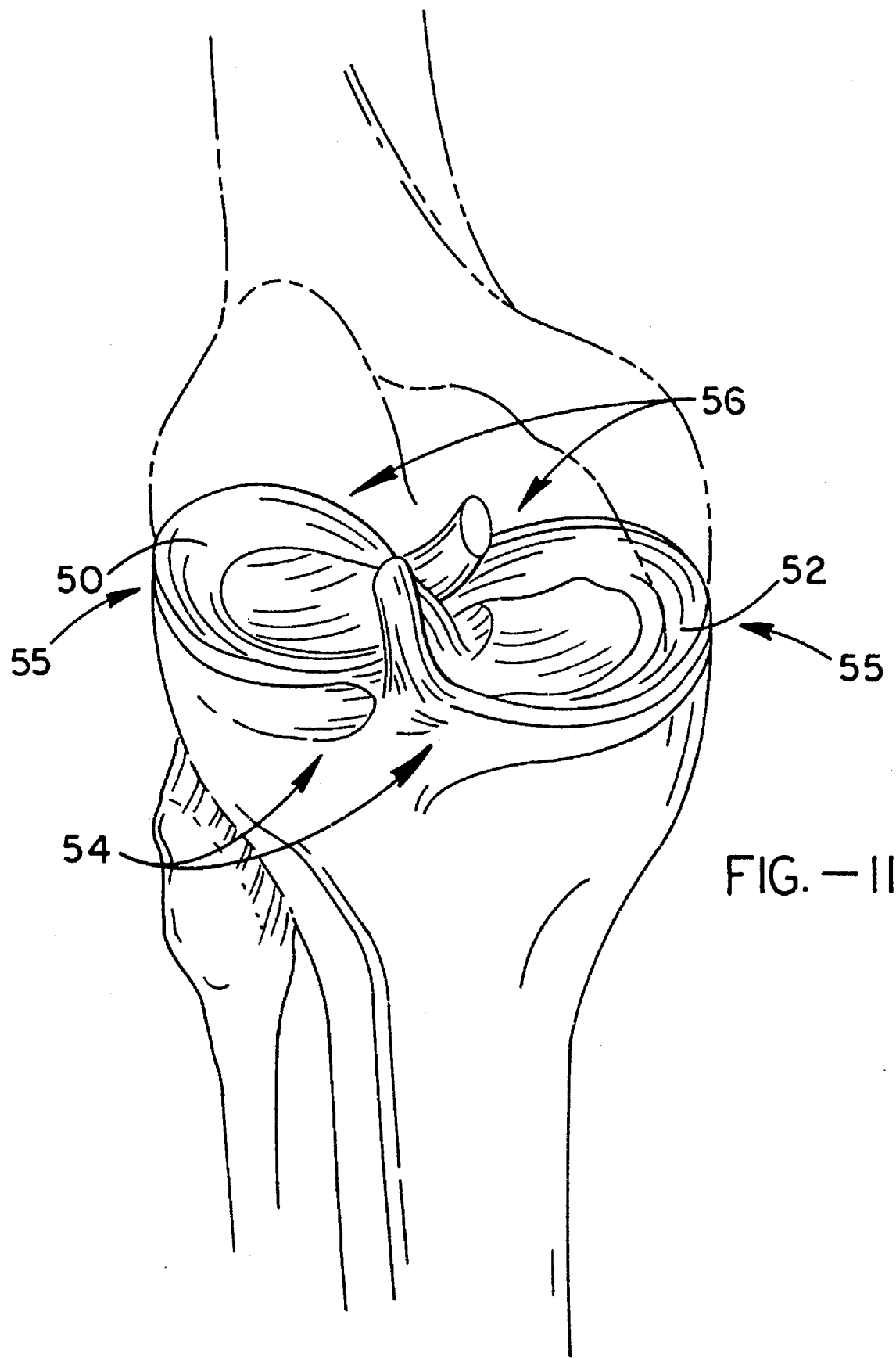
FIG. 11 is a perspective view of a human knee joint illustrating the left and right meniscus.

Referring to FIG. 8 through FIG. 10, the tomahawk embodiment of the curvilinear surgical punch of the present invention is shown. Referring again to FIG. 11, the tomahawk punch is adapted mainly to trim the anterior third 54 of the lateral and medial meniscus 50 and 52. The tomahawk embodiment can be manufactured in left and right configurations for operating upon the medial and lateral meniscus, respectively. As illustrated in FIG. 8 through FIG. 10, the tomahawk punch possesses pronounced angles along the intersection of sides 40, 42 and 40, 44 of the cutting head. The size of the angles applied to the intersections between sides 40, 42 and 40, 44 are limited only by the practical requirements of the invention, and can be obtuse, right, or acute, but a range from 110 degrees to 135 degrees is preferred. Also, there is no requirement that the angles applied to the intersections between sides 40, 42 and 40, 44 be equivalent. The angles applied to sides 40, 42 and 40, 44 allows the tomahawk shape to conform to the anterior third 54 of meniscus 50 or 52 in a superior fashion. Note also, that preferably sides 40, 44 include cutting edges to provide for greater versatility of the punch.

It is also anticipated that all three embodiments, the standard, sidebiting, and tomahawk, as shown in FIG. 2 through FIG. 4, FIG. 5 through FIG. 7, and FIG. 8 through FIG. 10, respectively, be represented in left-swept, right-swept and upswept configurations. These configurations can be achieved by shaping support means 20 in a left-swept, right-swept, or up-swept manner. The left-swept, right-swept, or up-swept configurations will allow for a wider range of access of the curvilinear surgical punch 10 to the meniscal tissue. Additionally, a wide range of lengths for the arcuate edges 26 and 28 of upper blade member 22 and lower frame member 24, respectively, are acceptable.

In FIG. 12 through FIG. 14, the advantages of the present invention over previous punch-type devices in achieving a smooth meniscal remnant is shown. In FIG. 12, a widely used punch-type device is shown. In FIG. 13, the punch of FIG. 12 is shown operating on the middle third 55 of left meniscus 52, and in FIG. 14 the present invention is depicted operating upon the middle third 55 left meniscus 52. A characteristic of cutting the meniscus 52, is that raised edges 60 result. The raised edges 60 are the result of meniscal tissue that is missed between the junction of successive "bites" 62. The raised edges 60 must be trimmed, or else they will abrade inside the patient's joint and cause irritation. As depicted in FIG. 13, the conventional surgical punch requires numerous bites 62 upon the meniscus 52 to remove the same amount of meniscal tissue that the present invention removes with a fewer number of bites 62 as illustrated in FIG. 14. In comparing FIG. 13 to FIG. 14, it can be seen that more raised edges 60 result from the conventional device than with the present invention since the present invention requires fewer bites 62 than the conventional device, resulting in fewer raised edges 60. The reason the present invention requires fewer bites 62 than the conventional device, is because arcuate edges 26 and 28, shown in FIG. 2 through FIG. 10, have a greater curve length than the cutting surfaces of the conventional device depicted in FIG. 12. Also the curvilinear cutting surface of the present invention has a much more gradually curving surface than that of the ellipsoid surfaces which characterize conventional surgical punches adapted for meniscal surgery. The gradual, sweeping nature of the curvilinear surface of the present invention creates a smoother surface with fewer bites 62 than previous meniscal surgery devices.

The greater number of bites 62 applied when using conventional devices, necessitates a greater number of surgical passes to remove raised edges 60. In FIG. 13 and FIG. 14, the area defined by dotted line 64 represents a quantity of meniscal tissue to be removed during a typical surgical procedure. By comparing FIG. 13 and FIG. 14, it can be seen that the quantity of tissue removed is greater with the present invention than with a conventional device. By further comparing FIG. 13 to FIG. 14, it can readily be seen how a greater number of passes is required by a conventional device to remove the same amount of meniscal tissue as the present invention removes in one or two passes.

It is also a standard procedure in meniscal surgery to further smooth out the trimmed area with a mechanical rotary trimmer, following use of a surgical punch. In comparing the resulting surface left by the previous device shown in FIG. 13 with the resulting surface of the present invention shown in FIG. 14, it can be readily seen that the smoother surface left by the present invention, would require a much less timely and rigorous application of the mechanical rotary trimmer than the rougher surface left by the previous device. Therefore, the present invention achieves a smoother meniscal remnant in less time than previous punch-type devices, due to both the decreased number of surgical passes required and the less timely application of the mechanical rotary trimmer.

FIG. 13 and FIG. 14 illustrate an additional advantage of the present invention over the previous devices used in meniscal surgery. A hatched region 66 shown in FIG. 13 and FIG. 14 illustrates an area which is difficult to reach with the previous devices. Because the previous devices could not reach hatched region 66, this region could break free following surgery, thus creating additional hardship for the patient and often necessitating an additional surgery to remove. FIG. 13 depicts the problems inherent with the previous devices in being unable to reach hatched region 66. As can be seen, prior art punches do not leave a smooth, stable rim along the anterior horn of the meniscus. FIG. 14 depicts the present invention being especially suited for reaching hatched region 66, thus alleviating any future hardship to the patient as a result of failing to trim this particularly troublesome region.

Accordingly, it will be seen that this invention provides a curvilinear surgical punch with a blade member having an arcuate edge with a wide convex surface. The length and shape of this arcuate surface combine to offer a surgical punch which creates superiorly smooth meniscal remnants in less time, with fewer surgical passes, than previous punch-type meniscal surgery instruments. This invention can also be adapted to a variety of shapes and configurations which offer favorable advantages in operating on both the anterior third and posterior third of the medial or lateral meniscus.

Although the description above contains many specificities, these should not be construed as limiting the scope of the invention but as merely providing illustrations of some of the presently preferred embodiments of this invention. Thus the scope of this invention should be determined by the appended claims and their legal equivalents.

I claim:

1. A surgical punch for cutting meniscal tissue, comprising:

(a) a substantially planar lower frame member, said lower frame member having a proximal end and a distal end, said lower frame member including a cavity;

(b) an upper blade member, said upper blade member having a proximal end and a distal end, said upper blade member having a length and a width, said proximal end of said upper blade member pivotally coupled to said proximal end of said frame member, said upper blade member having a top surface and a bottom surface, said top surface lying in a first plane, said bottom surface lying in a second plane, said first and second planes being substantially parallel, said bottom surface being continuously planar across the entire length and width of said upper blade member, said upper blade member including first and second rectilinear edges, said upper blade member including a curvilinear edge which is honed between said first and second planes, said curvilinear edge extending from said proximal end to said distal end of said upper blade member; and (c) support means for supporting said upper blade member and said lower frame member and for articulating said upper blade member in relation to said lower frame member between an open position and a closed position wherein said upper blade member is received in said cavity in said lower frame member in said closed position and wherein said lower frame member and said top and bottom surfaces of said upper blade member lie in substantially parallel planes in said closed position.

2. A curvilinear surgical punch, comprising:

(a) a lower frame member, said lower frame member having a proximal end and a distal end, said lower frame member being substantially planar from said proximal end to said distal end, said lower frame member including a cavity;

(b) an upper blade member, said upper blade member having a proximal end and a distal end, said upper blade member having a length and a width, upper blade member being substantially planar from said proximal end to said distal end, said proximal end of said upper blade member pivotally coupled to said proximal end of said lower frame member;

(c) said upper blade member having a top surface and a bottom surface, said top surface lying in a first plane, said bottom surface lying in a second plane, said first and second planes being substantially parallel, said bottom surface being continuously planar across the entire length and width of said upper blade member, said upper blade member including first and second rectilinear edges, said upper blade member including a curvilinear edge which is honed between said first and second planes, said curvilinear edge extending from said proximal end to said distal end of said upper blade member; and (d) support means for supporting said upper blade member and said lower frame member and for articulating said upper blade member in relation to said lower frame member between an open position and a closed position wherein said upper blade member is received in said cavity in said lower frame member in said closed position and wherein said lower frame member and said top and bottom surfaces of said upper blade member lie in substantially parallel planes in said closed position.

3. A surgical instrument, comprising:

(a) a lower frame member having a proximal end and a distal end, said lower frame member being substantially planar from said proximal end to said distal end, said lower frame member including a cavity;

(b) an upper blade member having a proximal end and a distal end, said upper blade member having a length and a width, said upper blade member being substantially planar from said proximal end to said distal end, said proximal end of said upper blade member pivotally coupled to said proximal end of said lower frame member;

(c) support means for supporting said upper blade member and said lower frame member and for articulating said upper blade member in relation to said lower frame member between an open position and a closed position wherein said upper blade member is received in said cavity in said lower frame member in said closed position and wherein said upper blade member and said lower frame member lie in substantially parallel planes in said closed position; and (d) said upper blade member having a top surface and a bottom surface, said top surface lying in a first plane, said bottom surface lying in a second plane, said first and second planes being substantially parallel, said bottom surface being continuously planar across the entire length and width of said upper blade member, said upper blade member including first and second rectilinear edges, said upper blade member including a curvilinear edge which is honed between said first and second planes, said curvilinear edge extending from said proximal end to said distal end of said upper blade member.

4. An apparatus as recited in claim 1, 2 or 3, wherein said first and second rectilinear edges are substantially perpendicular and wherein said curvilinear edge extends between said first and second rectilinear edges.

5. An apparatus as recited in claim 1, 2 or 3, wherein said first and second rectilinear edges are substantially perpendicular and wherein said curvilinear edge extends between said first and second rectilinear edges, said first and second rectilinear edges intersecting at a corner having an angle.

6. An apparatus as recited in claim 5 wherein said angle is an obtuse angle.

7. An apparatus as recited in claim 5 wherein said angle is a right angle.

8. An apparatus as recited in claim 5 wherein said angle is an angle other than a right angle.

9. An apparatus as recited in claims 1, 2 or 3, wherein said upper blade member includes a third rectilinear edge, at least two of said rectilinear edges intersecting each other at a corner having an angle.

10. An apparatus as recited in claim 9 wherein said angle is an obtuse angle.

11. An apparatus as recited in claim 9 wherein said angle is a right angle.

12. An apparatus as recited in claim 9 wherein said angle is an angle other than a right angle.

* * * * *